(12) United States Patent
Ziger

(10) Patent No.: US 7,099,018 B2
(45) Date of Patent: Aug. 29, 2006

(54) MEASUREMENT OF OPTICAL PROPERTIES OF RADIATION SENSITIVE MATERIALS

(75) Inventor: David Ziger, San Antonio, TX (US)

(73) Assignee: Infineon Technologies AG, Munich (DE)

(*) Notice: Subject to any disclaimer, the term of this patent is extended or adjusted under 35 U.S.C. 154(b) by 276 days.

(21) Appl. No.: 10/755,420

(22) Filed: Jan. 12, 2004

(65) Prior Publication Data

US 2005/0151962 A1    Jul. 14, 2005

(51) Int. Cl.
    *G01B 11/28*    (2006.01)
(52) U.S. Cl. .................................................. 356/630
(58) Field of Classification Search .................. None
    See application file for complete search history.

(56) References Cited

U.S. PATENT DOCUMENTS

| | | | |
|---|---|---|---|
| 4,977,330 A | | 12/1990 | Batchelder et al. |
| 5,241,366 A | * | 8/1993 | Bevis et al. ................. 356/632 |
| 5,409,538 A | * | 4/1995 | Nakayama et al. ......... 118/688 |
| 6,567,213 B1 | * | 5/2003 | Rosencwaig et al. ....... 359/369 |

2002/0090743 A1    7/2002    Johnson et al.

FOREIGN PATENT DOCUMENTS

WO    WO 03/025497 A1    3/2003

OTHER PUBLICATIONS

Diamond, William J., "Practical Experiment Designs for Engineers and Scientists," pp. 25-33, Van Nostrand Reinhold Company, Inc., New York 1981.
Wolf, S. and Tauber, R.N., "Silicon Processing for the VLSI Era," vol. I: Process Technology, 2nd Ed., pp. 488-491, Lattice Press, Sunset Beach, CA, 2000.

* cited by examiner

*Primary Examiner*—Michael P. Stafira
(74) *Attorney, Agent, or Firm*—Slater & Matsil, L.L.P.

(57) ABSTRACT

A system and method for measuring optical properties of films deposited or formed on semiconductor wafers. Measurements of an optical property are made in a plurality of non-overlapping locations within a test region of a film at a low radiation dose, and the measurements are averaged. The radiation dose is less than the actinic radiation sensitivity dose of the film, so that chemical changes in the film are not caused by the measurements. The measurements may be calibrated to prior art methods, and the results may be adjusted by the adjustment or calibration factor.

30 Claims, 4 Drawing Sheets

MEASUREMENT OF OPTICAL PROPERTIES OF RADIATION SENSITIVE MATERIALS

TECHNICAL FIELD

The present invention relates generally to a system and method of testing semiconductor wafers, and more particularly to a system and method of measuring optical properties of films formed on a semiconductor wafer.

BACKGROUND

Semiconductor devices are used in a variety of electronic applications, such as personal computers, cell phones, digital cameras, and other electronic equipment, as examples. There may be millions of transistors and capacitors formed on a single integrated circuit (IC), for example. Semiconductor devices are fabricated by depositing various material layers over a semiconductor wafer, such as conductors, semiconductors, and insulators, and patterning the various material layers to form circuit elements and interconnects therebetween.

The various material layers of semiconductor devices are typically patterned using lithography techniques to create components and circuits. In semiconductor lithography, a resist is deposited or spin-coated onto a wafer substrate, and is selectively exposed to a form of radiation, such as ultraviolet light, electrons, or x-rays, as examples. An exposure tool and mask are typically used to effect the desired selective exposure. Patterns in the resist are formed when the wafer undergoes a subsequent development step. The areas of resist remaining after development protect the substrate regions that they cover during subsequent processing. Locations from which resist has been removed can then be subjected to a variety of subtractive (e.g., etching) or additive (e.g., ion implantation) processes that transfer the pattern onto the substrate surface. The areas of the resist exposed to the energy are made either soluble or insoluble in a specific solvent known as a developer. In the case where the irradiated (exposed) regions are soluble, a positive image of the mask is produced in the resist, referred to as a positive resist. If the non-irradiated regions are dissolved by the developer, a negative image results in the resist, referred to as a negative resist.

There may be 20 or more masking layers used to manufacture an advanced integrated circuit, for example. The trend in semiconductor technology is towards scaling down the size of semiconductor devices, for increased speed and decreased power consumption, as examples. For smaller-scale semiconductor devices, resists are typically used that are exposed at 248 nm or 193 nm wavelengths. The term "actinic" refers to the wavelength of the radiant energy, especially in visible and ultraviolet regions of the light spectrum, by which photochemical changes are produced in a radiation sensitive resist.

A resist typically comprises three components: a resin or matrix material that functions as a binder; an active ingredient or photoactive compound (PAC); and a solvent, which maintains the resist material in a liquid state until it is applied to a semiconductor wafer. The photoactive component of a resist is the component of a resist material that undergoes a chemical reaction in response to actinic radiation.

Optical properties are fundamental to understanding the response of semiconductor materials to radiation, such as in the exposure of resists. Simulation and modeling require knowledge and characterization of optical properties of a film in order to predict processing results under various processing conditions. Therefore, measurement of optical properties of films used in semiconductor manufacturing is important in simulating the results that are obtainable with photolithography.

An important optical property that impacts patterning is the index of refraction of a resist material, as an example. It is therefore important to have the capability to measure optical properties such as the real component (RI) and imaginary component (k) of the refractive index at the actinic or exposure wavelengths of films formed on semiconductor wafers. Often the variation of the refractive index of a film across the surface of a wafer is of interest, so many measurements are taken at many locations across the wafer, e.g., 49 measurements may be made across a wafer.

A significant problem with measuring optical properties of radiation sensitive resist materials is that the measurement method usually requires that the material be probed with a beam of radiation at the wavelength for which the material is labile or unstable. Consequently, the accurate measurement of film properties at the actinic wavelength of a film can cause chemical and/or physical changes to the material. Portions of films deposited on semiconductor wafers may be exposed during the measurement and testing process, which prohibits the films from being usable as material layers or pattern-generating resists, as examples. Thus, what is needed in the art is a method and system for measuring optical properties, such as the refractive index, of films deposited on a semiconductor wafer, that do not cause chemical changes to the films.

SUMMARY OF THE INVENTION

These and other problems are generally solved or circumvented, and technical advantages are generally achieved, by preferred embodiments of the present invention, which provide a system and method of measuring optical properties of films deposited on a semiconductor workpiece. An optical property of a region of a film deposited on a semiconductor wafer is measured at a first location at a dose less than the exposure dose of the film, and the optical property of the region of the film is also measured in at least one second location in the region at a dose less than the exposure dose of the film, wherein the second location is different from yet proximate the first location. The measurement results of the first location and the at least one second location are averaged to find an average measurement result of the optical property for the region of the film. The non-overlapping plurality of measurements may be repeated in a number of regions of the film deposited over the wafer. A first film may be measured using both a prior art method and the method described herein to determine an adjustment or calibration factor. A second film may then be measured using the present method, and the measurement results may then be adjusted by the adjustment factor.

In accordance with a preferred embodiment of the present invention, a method of measuring an optical property of a film includes providing a workpiece, the workpiece having a film disposed thereon, measuring an optical property of the film in a first location, and measuring the optical property of the film in at least one second location, each second location being proximate and different from the first location, the first location and the at least one second location comprising a first region of the film. The optical property measurement of the film in the first location and the optical property measurement of the film in the at least one second location of the film are averaged to determine an average optical property measurement of the first region of the film.

In accordance with another preferred embodiment of the present invention, a system for measuring an optical property of a film includes a radiation reduction element, and a radiation transceiver disposed proximate the radiation reduction element. The radiation transceiver includes a radiation transmitter for emitting a radiation dose towards a film disposed on a device. The radiation transceiver includes a radiation detector for measuring reflected radiation from the film in a first location and in at least one second location using a reduced radiation dose, each second location being proximate and different from the first location, the first location and the at least one second location comprising a first region of the film, the reduced radiation dose comprising the radiation dose emitted from the radiation transceiver reduced by the radiation reduction element. The system includes a processor, wherein the processor is adapted to average the measured optical property of the film in the first location and the measured optical property of the film in the at least one second location to determine an average optical property measurement of the first region of the film.

In accordance with yet another embodiment of the present invention, a system for measuring an optical property of a film includes means for transmitting radiation towards a film disposed on a device, means for controllably reducing the radiation transmitted from the means for transmitting radiation, and means for measuring radiation transmitted from the means for transmitting radiation, reduced by the means for controllably reducing the radiation and reflected from the film disposed on the device in a first location and in at least one second location, each second location being proximate and different from the first location, each second location being proximate and different from every other second location, the first location and the at least one second location comprising a first region of the film. The system includes means for averaging the measured optical property of the film in the first location and the measured optical property of the film in the at least one second location to determine an average optical property measurement of the first region of the film Advantages of embodiments of the invention include providing the ability to accurately measure optical properties of radiation sensitive film without causing chemical changes in the film. Many measurements are taken at low, short doses in very close proximity to one another in a particular region of the film, so that the signal-to-noise ratio is lower than if measuring optical properties of films that are stable. Optical properties such as the index of refraction may be measured using embodiments of the present invention. The plurality of low-dose measurements may be taken in a plurality of regions across a surface of a workpiece to determine the variation of the refractive index of a film across the surface of a workpiece, for example. The measurements taken in accordance with embodiments of the present invention may be used late in simulation of lithography of the measured films for modeling purposes, for example. By distributing the measurement dose of radiation across a larger surface area of the surface of a film in accordance with embodiments of the present invention, chemical changes to the film caused by the measurements of the film are avoided.

The foregoing has outlined rather broadly the features and technical advantages of embodiments of the present invention in order that the detailed description of the invention that follows may be better understood. Additional features and advantages of embodiments of the invention will be described hereinafter, which form the subject of the claims of the invention. It should be appreciated by those skilled in the art that the conception and specific embodiments disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

Corresponding numerals and symbols in the different figures generally refer to corresponding parts unless otherwise indicated. The figures are drawn to clearly illustrate the relevant aspects of the preferred embodiments and are not necessarily drawn to scale.

DETAILED DESCRIPTION OF ILLUSTRATIVE EMBODIMENTS

The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

The present invention will be described with respect to preferred embodiments in a specific context, namely, a semiconductor wafer or workpiece. The invention may also be applied, however, to films deposited or formed on other objects, for example. Embodiments of the present invention are preferably used to measure optical properties of labile or radiation sensitive materials, although embodiments of the present invention also have application in the measurements of optical properties of stable or radiation insensitive materials.

The refractive index is an optical property of a material such as a film. The refractive index is the complex sum of two components, RI (real) and k (imaginary):

$$n = RI + (i \cdot k),$$

wherein the real component, RI, is the ratio of the speed of radiation through a vacuum to the speed of radiation through the medium of interest. The component k is the imaginary part, which is related to the amount of light or energy that is absorbed or lost by the medium or film.

In the prior art, to measure the refractive index, energy is directed towards a film, and the response of the material is measured. For example, when dealing with films disposed over substrates that comprise a semiconductor material such as silicon, a light impinges on the film, and a periodic pattern of intensity vs. wavelength or incident angle is reflected back, known as standing waves. From the standing waves, the refractive index of the film can be calculated as a function of wavelength. The refractive index is typically wavelength-dependent.

Figure 1:
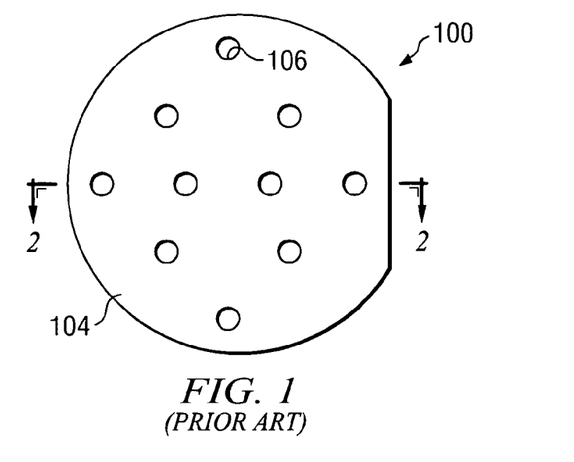
FIG. 1 shows a top view of a semiconductor wafer with a film deposited thereon, wherein optical properties of the film are measured at a plurality of locations in accordance with a prior art method.
Figure 2:
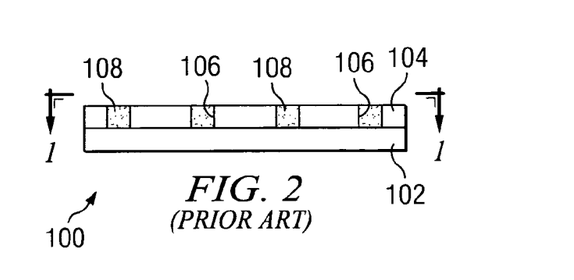
FIG. 2 shows a cross-sectional view of the wafer shown in FIG. 1, wherein the measurements cause chemical changes in the film.

A semiconductor device 100 comprising a workpiece 102 with a film 104 deposited thereon is shown in a top view in FIG. 1 and in a cross-sectional view in FIG. 2. In a prior art method, to measure the refractive index of the film 104, a light such as UV light is directed towards the workpiece 102 in a plurality of test regions 106. Light reflected from the film 104 is measured to determine the refractive index of the film 104.

Accurate measurement of optical properties is based on optimizing the signal to noise ratio of the response to a given measurement. Often, to decrease the experimental error of a measurement method and to decrease measurement time, a relatively large dose of light must be used. If the film 104 is stable to the actinic radiation, such as an oxide material or nitride material, a large dose of light is not problematic. Although a measurement dose of light at 157 nm may be large, it causes no appreciable change in the physical properties of these films. However, if the film 104 to be measured is sensitive to the integrated measurement dose of light, then the dose of light required to accurately measure the property can cause chemical reactions 108 in the film, as shown in FIG. 2, which shows a cross-sectional view of the workpiece 102 of FIG. 1. High doses of light cause photochemical reactions in portions 108 of the film 104 in the measurement areas, which may change physical properties such as the refractive index of the film 104. Changing physical properties of the film 104 is undesirable because experimental error is introduced: it is undesirable for the measurement to modify the sample being measured.

Embodiments of the present invention achieve technical advantages by providing a system and method for measuring optical properties of a film that does not cause chemical reactions in the film. A low dose of radiation, e.g., less than the actinic radiation sensitivity dose or exposure dose of the film, that will not cause chemical reactions in the film, is used to measure the optical properties of the film, and the measurements are repeated in a plurality of non-overlapping locations, such that the average of the multiple measurements provides an accurate estimate of the optical property of interest.

Figure 3:
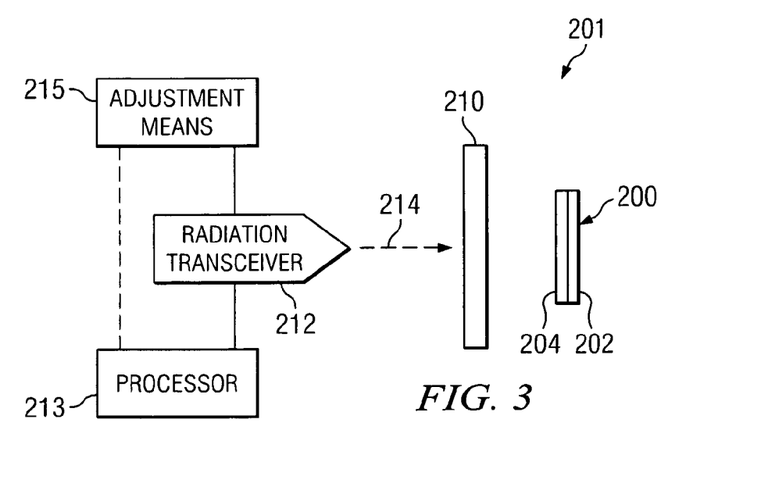
FIG. 3 shows a schematic diagram of a system for measuring films formed on semiconductor wafers in accordance with an embodiment of the present invention.

A system 201 for measuring optical properties of a film 204 in accordance with an embodiment of the present invention is shown in FIG. 3. An optional radiation reducer 210 may be disposed between a device 200 and a radiation transceiver 212. The radiation transceiver 212 may be coupled to an optional processor 213 that is adapted to perform calculations of calibrating, measuring and averaging the optical properties, to be described further herein.

In one embodiment, the device 200 comprises a semiconductor device, including a workpiece 202 with a film 204 formed thereon. The workpiece 202 may include a semiconductor substrate comprising silicon or other semiconductor materials covered by an insulating layer, for example. The workpiece 202 may also include other active components or circuits, not shown. The workpiece 202 may comprise silicon oxide over single-crystal silicon, for example. The workpiece 202 may include other conductive layers or other semiconductor elements, e.g., transistors, diodes, etc., not shown. Compound semiconductors, GaAs, InP, Si/Ge, or SiC, as examples, may be used in place of silicon. The device 200 may alternatively comprise other types of objects having a film 204 formed thereon, for example. The device 200 may comprise a printed circuit board (PCB) or a metal having a film 204 disposed on a surface thereof, as examples, or alternatively, the device 200 may comprise other objects having a film 204 deposited or formed thereon, wherein it is desired to measure the optical properties of the film 204.

The radiation transceiver 212 is adapted to transmit and receive radiation 214, which may be in the form of light or other energy, as examples. The radiation transceiver 212 may be adapted to transmit and receive ultraviolet light, electrons, or x-rays, as examples, although the radiation 214 may alternatively comprise other types of energy. The radiation transceiver 212 may comprise two separate and discrete components: a radiation transmitter such as a light source, and a means of measuring radiation reflected from the film, or a radiation receiver, such as a spectraphotometer, as examples, not shown.

The optional radiation reducer 210 comprises a screen in one embodiment, wherein the screen decreases the radiation 214 transmitted from the radiation transceiver 212 during the measuring of the optical properties of the film 204. In another embodiment, the radiation reducer 210 comprises a filter adapted to reduce the amount of radiation from the radiation transceiver 212. In yet another embodiment, the radiation reducer 210 comprises an opaque material such as a metal having one or more apertures formed therein. The radiation reducer 210 may alternatively comprise other devices adapted to reduce the transmitted radiation 214 from the radiation transceiver 212 while the optical properties of the film 204 are measured.

The radiation 214 transmitted from the radiation transceiver 212 may alternatively be reduced using an optional adjustment means 215 coupled to (or part of, not shown) the radiation transceiver 212, as shown. The amount of radiation 214 emitted from the transceiver 212 may be decreased manually using the adjustment means 215 operable by an operator (not shown) of the system 201 or electronically by a processor 213. The adjustment means 215 may reduce the radiation transmitted from the radiation transceiver 212 by decreasing the radiation amplitude or by decreasing the time the film 204 is irradiated, as examples.

Preferably, in one embodiment, the radiation reducer 210 and/or adjustment means 215 are adapted to reduce the radiation 214 transmitted from the radiation transceiver 212 to about 50 to 90% of the actinic radiation that causes noticeable chemical reactions to occur in the film, referred to herein as the actinic radiation sensitivity dose.

The system 201 is designed such that measurements of an optical property may be made in a plurality of locations and/or regions of a workpiece 202. For example, the radiation transceiver 212 may be stationary, and the workpiece 202 may be moved by a stepper or other device to the various test locations. Alternatively, the workpiece 202 may be stationary, and the radiation transceiver 212 may be moved by a stepper or other device to the various test locations. Or, both the transceiver 212 and workpiece 202 may be movable within the system 201, for example.

Figure 4:
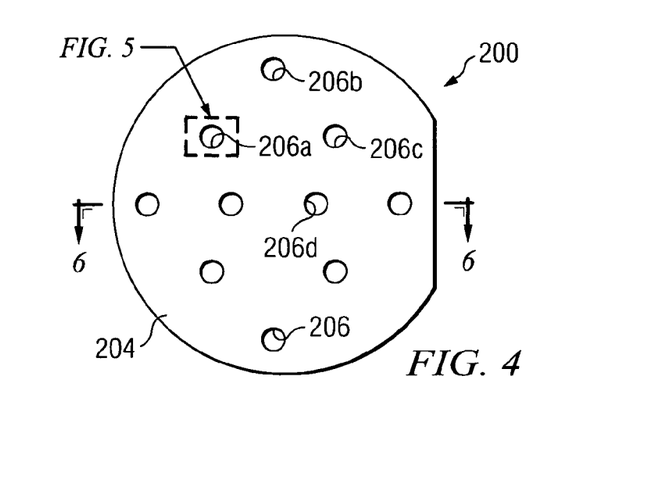
FIG. 4 illustrates a top view of a semiconductor wafer with a film deposited thereon, wherein optical properties of the film may be measured at one or more locations in accordance with an embodiment of the present invention.
Figure 5:
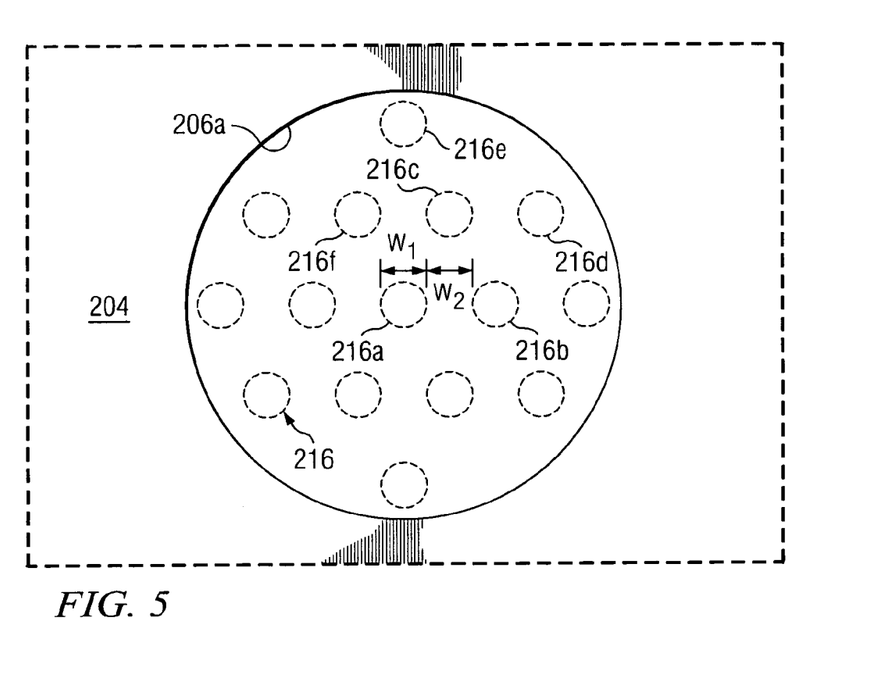
FIG. 5 shows a more detailed view of one measurement location of FIG. 4, illustrating that a plurality of measurements are taken in the measurement location at a dose less than the actinic radiation sensitivity dose of the film.
Figure 6:
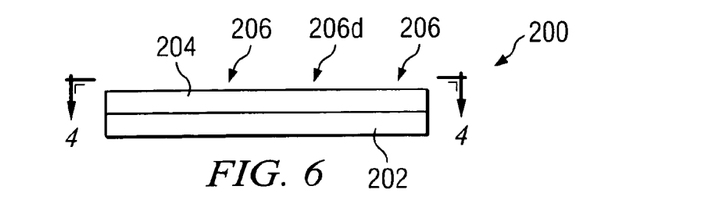
FIG. 6 is a cross-sectional view of the wafer of FIG. 4, wherein the plurality of measurements made in each location of the wafer does not cause chemical reactions in the film.

In accordance with embodiments of the present invention, measuring an optical property such as the refractive index of a film 204 includes providing device 200 including a workpiece 202, the workpiece 202 having a film 204 disposed thereon, as shown in FIGS. 4 through 6. FIG. 4 shows a top view of the device 200 and FIG. 6 shows a cross-sectional view of the device 200. FIG. 5 shows a more detailed view of a region 206 of the device 200 shown in FIG. 4.

The film 204 preferably comprises a thickness of about 1.5 µm or less, and more preferably comprises a thickness of about 0.05 µm to about 0.5 µm, as examples. The film 204 may alternatively comprise other thicknesses. In accordance with embodiments of the present invention, the film 204 comprises a first region 206a and at least one second region 206b, 206c, 206d, etc. An optical property of the film 204 is measured in a first location 216a of the first region 206a, as shown in FIG. 5. The optical property of the film 204 is measured in at least one second location 216b, 216c, 216d, 216e, 216f, etc., of the first region 206a, each second location 216b, 216c, 216d, 216e, 216f, etc., being proximate and different from the first location 216a. Each second location 216b, 216c, 216d, 216e, 216f, etc., is preferably also proximate and different from every other second location 216b, 216c, 216d, 216e, 216f, etc., within the first region 206a. The measurement of the optical property of the film 204 in the first location 216a and measurement of the optical property of the film 204 in the at least one second location 216b, 216c, 216d, 216e, 216f, etc. of the film 204 are then averaged (e.g., by the processor 213 of FIG. 3) to determine an average optical property measurement of the first region 206a of the film 204.

The first location 216a and the at least one second location 216b, 216c, 216d, 216e, 216f, etc. of the film 204 comprise a spot size width $W_1$. The spot size may comprise a circular or oval pattern, as shown, although the spot size may comprise a square, rectangle or other shapes, as examples. Each first location 216a and each at least one second location 216b, 216c, 216d, 216e, 216f, etc. are located in a unique measurement location, without overlapping any other measurement location 216a, 216b, 216c, 216d, 216e, 216f, etc. For example, each first location 216a and each at least one second location 216b, 216c, 216d, 216e, 216f, etc. of the film 204 are preferably located a width $W_2$ away from each other measurement location 216a, 216b, 216c, 216d, 216e, 216f, etc., wherein the width $W_2$ is preferably greater than or equal to the measurement spot size width $W_1$.

The optical property measurements made at the plurality of locations 216a, 216b, 216c, 216d, 216e, 216f, etc., are preferably made at a radiation dose less than the actinic radiation sensitivity dose of the film 204. For example, measuring the optical property of the film 204 in locations 216a, 216b, 216c, 216d, 216e, 216f, etc., may be made at a radiation dose of about 50 to 90% of the actinic radiation sensitivity dose of the film 204. If the film 204 comprises a stable material having no actinic radiation dose, then the radiation dose is preferably less than the usual dose used in the prior art to measure the optical property of the film 204, for example.

To determine the dose of radiation to be used, first, the actinic radiation sensitivity dose of the film 204 is determined. The actinic radiation sensitivity dose or exposure dose of radiation of the film 204 may be obtained from the manufacturer of the film 204, for example. Or, an infrared spectrum of the film 204 may be measured before and after it has been exposed, and the film 204 may be examined to determine when the chemical bonds begin to break, for example. The actinic radiation sensitivity dose may be determined, for example, by determining the minimum dose required to chemically alter the film 204 (e.g., if the film 204 comprises a radiation sensitive resist). This may be achieved by using an exposure tool to incrementally increase the dose. The radiation sensitive resist film 204 can then be developed, and a profiler can be used to determine at what dose a thickness loss occurs in a positive radiation sensitive resist film 204 (or at what dose a gain occurs, in a negative radiation sensitive resist film 204).

Second, the radiation dose emitted from the radiation transceiver 212 (FIG. 3) is determined. This radiation dose is then reduced by a certain factor to avoid chemically changing the film 204 during the measurements. For example, the dose of radiation to be used to measure the optical property of the film 204 may be adjusted, if necessary, to be less than the actinic radiation sensitivity dose of the film 204 either using the optional adjustment means 215 or the optional radiation reducer 210, or both. The maximum time for the measurement may also be determined, from the radiation transceiver 212.

The number of measurements N may be determined or calculated by considering the potential loss in measurement accuracy due to lower signal output in measurement. A map of the workpiece 202 surface may be made (e.g., using the processor 213 of FIG. 3) with sufficient space to accommodate the number of measurements N points, preferably conserving as small as possible of a space. Multiple measurements are taken in the reserved mapped area of the workpiece 202 surface under these selected conditions, and the plurality of measurements made in a particular test region 206 is averaged. The standard deviation and/or the distribution may also be calculated (again, e.g., using processor 213 of FIG. 3) to determine whether the uncertainty due to measurement noise is adequate. If the uncertainty is inadequate, then more measurements may be taken and averaged in to achieve the desired results. Because the radiation dose of the optical property measurements is less than the actinic radiation sensitivity dose of the film 204, more noise may be noticed in the measurements at the smaller doses. However, by averaging the plurality of measurements taken, a number of measurements N can be defined that are necessary to provide the required accuracy of the average measurements. Note that when the refractive index is the optical property being measured, small deviations in the average film thickness over the measurement area are not likely to have an effect on the measurement results, because the film thickness, n and k may be calculated independently.

Statistical analysis may be used to determine the number of measurements N to be taken, based on the distribution and the required precision, for the radiation dose at which the optical property measurements are taken. First, the distribution of the measurement at a particular measurement dose is determined. Then, well-known statistical methods may be used to determine the number of measurements that are required for accuracy within a predetermined range.

Figure 7:
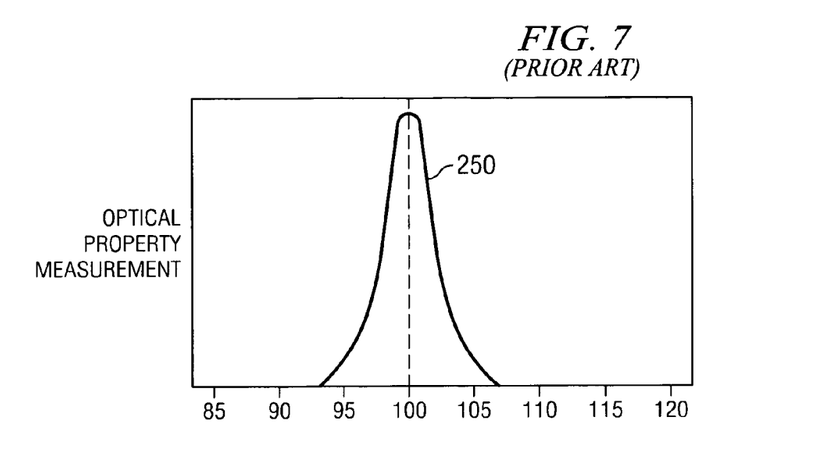
FIG. 7 shows a histogram of measurements made using a prior art method.

FIG. 7 shows an example of a population distribution 250 of optical property measurements taken using a prior art method with high radiation doses for a stable film 204. The population distribution 250 is a histogram plot of the measured results, with the y-axis representing the frequency or number of measurements obtained at a particular value along the x-axis. The numbers on the x-axis in FIG. 7–9 are exemplary; the numbers may actually represent the real, imaginary, or both the real and imaginary components of the refractive index or other optical property of a film, for example. The population distribution 250 is tight (e.g., the curve 250 is steep and narrow), and also has a tight signal-to-noise ratio, indicated by the relatively steep curve. For example, the vast majority of the measurements are between 95 and 105 for the population distribution 250 shown in FIG. 7.

Figure 8:
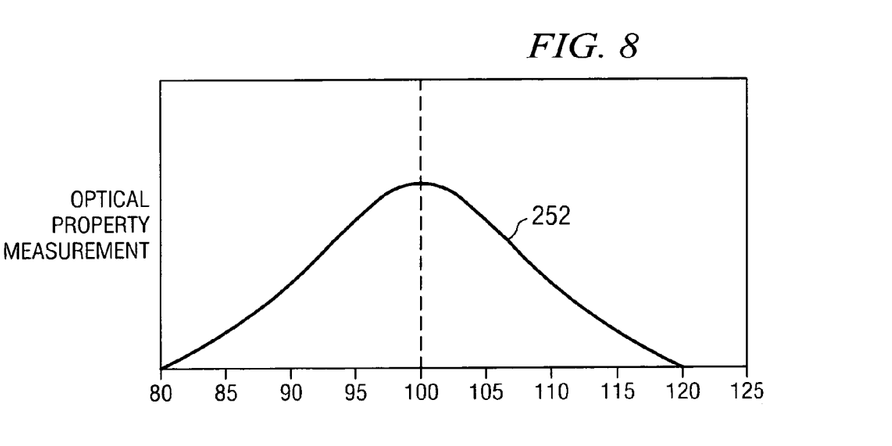
FIG. 8 shows a histogram of measurements made using the method described herein.

FIG. 8 shows an example of a population distribution 252 of optical property measurements taken using the method described herein with reduced radiation doses for either a radiation sensitive or stable film 204. The population distribution 252 is less tight (e.g., the curve 252 is less steep and is wider) than the distribution 250 in FIG. 7, and also has a less tight signal-to-noise ratio, indicated by the less steep curve. For example, the majority of the measurements are between 85 and 115 for the population distribution 252 shown in FIG. 8. This indicates that more measurements are needed in distribution 252 to obtain the same precision as the distribution 250 in FIG. 7. The index of refraction measurements along the x-axis may preferably be represented by $RI+(i \cdot k)$, for example.

Figure 9:
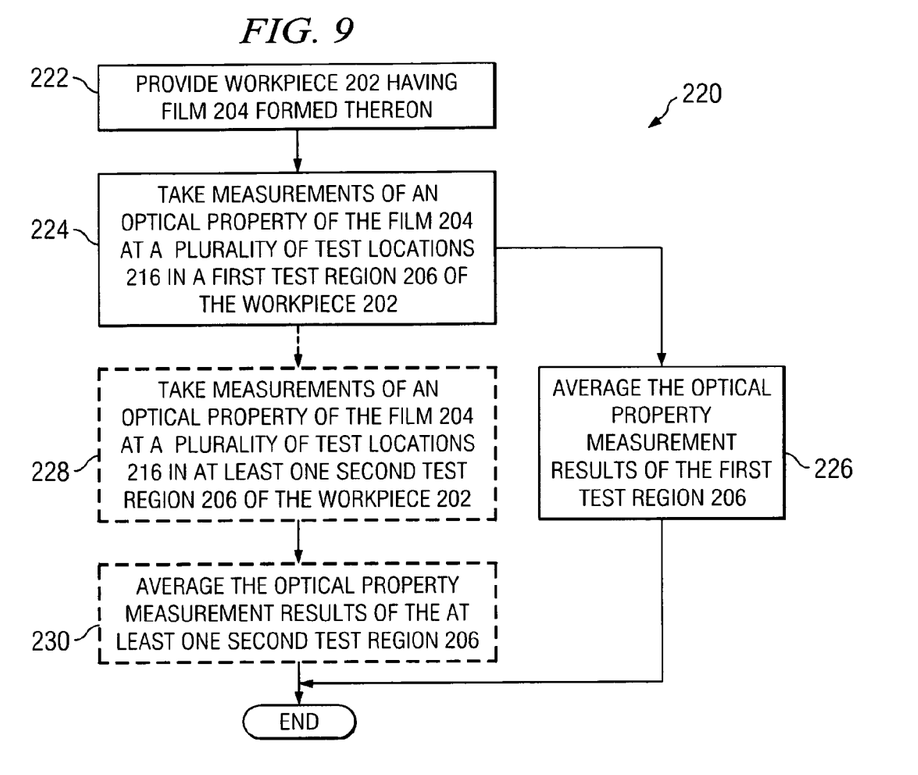
FIG. 9 is a flow chart illustrating methods of measuring optical properties of a film in accordance with embodiments of the present invention.

A flow chart 220 of a method in accordance with an embodiment of the present invention is shown in FIG. 9. First, a workpiece 204 is provided, having a film 204 formed thereon (step 222). Measurements of an optical property of the film 204 are taken at a plurality of test locations 216 in a first test region 206 of the workpiece 204 (step 224). The optical property measurement results are then averaged (step 226). This may be repeated in a plurality of test regions 206 of the film 204, to detect fluctuations in the optical property across the device 200. For example, measurements of an optical property may be taken at a plurality of test locations 216 in at least one second test region 206 (step 228). The measurement results of the optical property are then averaged for the at least one second test region (step 230).

Figure 10:
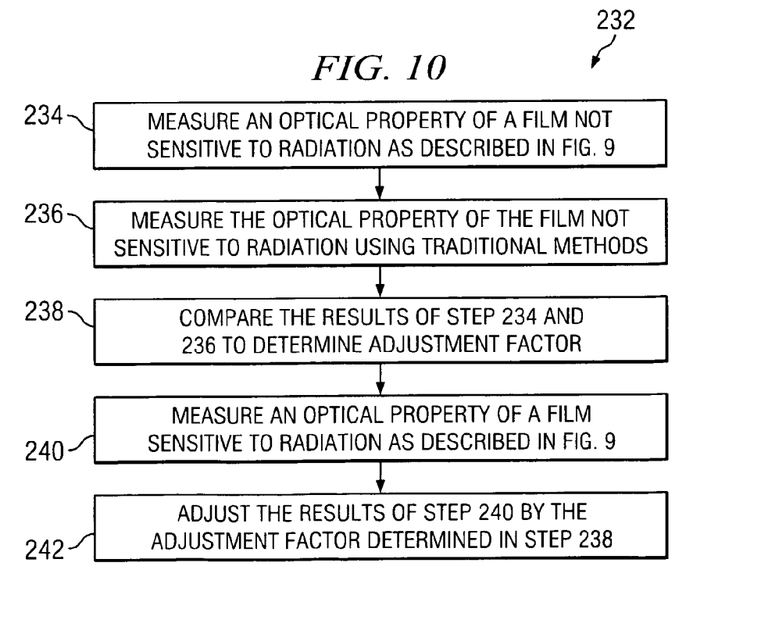
FIG. 10 is a flow chart illustrating how the measurement results of embodiments of the present invention may be calibrated using prior art methods.

Results of the optical property measurement method described herein may be calibrated to results of prior art measurement methods. An example of such a calibration technique is shown in the flow chart 232 of FIG. 10. An optical property of a film not sensitive to radiation is measured using an embodiment of the present invention, e.g., as described with reference to the flow chart 220 of FIG. 9 (step 234). An optical property of the film not sensitive to radiation is measured using traditional prior art methods (e.g. at a high dose of radiation), (step 236). The measurement results of step 234 and step 236 are compared to determine adjustment or calibration factor (step 238). An optical property of a film sensitive to radiation is then measured in accordance with an embodiment of the present invention, e.g., as described with reference to the flow chart 220 of FIG. 9 (step 240). The measurement results of step 240 are then adjusted by the adjustment factor determined in step 238 (step 242).

Figure 11:
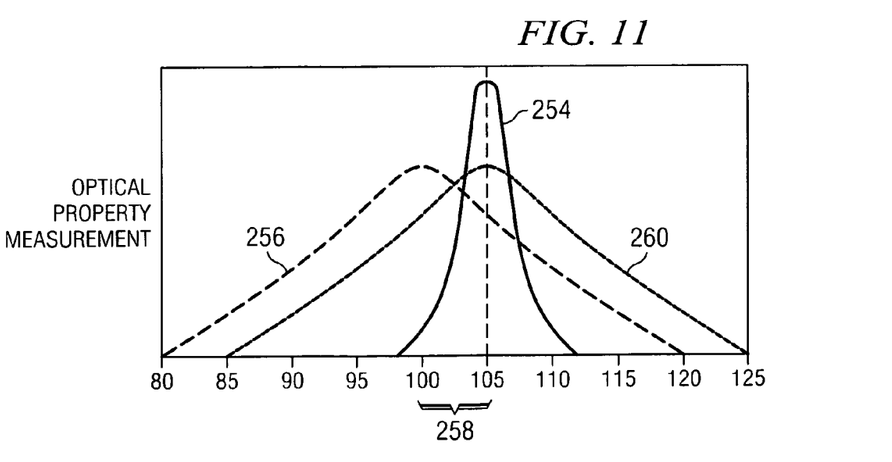
FIG. 11 shows a histogram of measurements made using the method described herein, calibrated using an adjustment factor in accordance with an embodiment of the present invention.

FIG. 11 illustrates that the distribution of the plurality of measurement results can be shifted according to an embodiment of the present invention by using a stable film to calibrate the optical property measurement technique described herein. For example, the stable material or film such as an oxide tested using a prior art method may have a distribution 254 with an average of 105, as shown in FIG. 11. The stable film is then tested using the present method described herein using a plurality of sub-actinic radiation sensitivity dose in each test region to achieve the distribution 256 having an average distribution of 100 having a less steep, wider curve. The amount of adjustment 258 (or calibration factor) needed to achieve the mean of the prior art test method results is then calculated or determined. Thus, a stable material can be used to calibrate a shift 258 to be made to the measurements taken in accordance with embodiments of the present invention, so that the present method can later be used for measuring optical properties of a non-stable material. A non-stable material may then be tested, and the average or mean results may be adjusted by the amount of adjustment 258 calculated. The adjustment 258 may be applied as a correction to the mean of the statistical results, for example. Note that in some applications, the amount of adjustment 258 may be zero, such as shown at 260. The processor 213 of the measurement system 201 shown in FIG. 3 may be adapted to apply the adjustment 258 or offset to the measured results of the optical property, for example.

An example of measuring the index of refraction of a film 204 comprising a radiation sensitive resist material in accordance with an embodiment of the present invention will next be described. Assume a radiation sensitive resist material 204 begins to degrade at 10 mJ/cm², and the radiation dose or beam of energy needed to accurately measure n and k impinges upon the film at 100 mJ/cm². In accordance with an embodiment of the present invention, filters or an aperture 210 (see FIG. 3) are used to reduce the dose for a single measurement to 5 mJ/cm². The filter or aperture 210 allows only a small portion of the beam to pass through. The accuracy of the measurement may be degraded, but the measurements can be repeated in unique, non-overlapping locations about 19 times, for example, shifting locations each time by a distance larger than the spot size or area being radiated. For example, the spot size may be 10×10 μm, and the location of a subsequent measurement spot may be shifted by about 20×15 μm. Note that because radiation sensitive films 204 are sensitive to accumulated doses of radiation, in order to achieve the advantages of embodiments of the present invention, preferably, the plurality of low radiation dose measurements are not taken in exactly the same spot, or otherwise the accumulated doses of radiation may chemically alter the film 204 being measured. From statistical analysis it is predicted that the average n and k will approach the true value of the measurement. The greater the number of measurements, the more accurate the measurement becomes, and the lower the signal-to-noise ratio. The dose for measurement can be reduced and the number of measurements increased, so as not to physically change the film 204 no matter how sensitive the film 204 is to radiation.

The processing effects of radiation sensitive film 204 may be monitored by measuring changes in optical properties. If the optical properties are radiation sensitive, then the methods of optical property measurement described herein can be performed before and after multiple processes. In this case, the area of the film 204 measured would necessarily need to be expanded. To mitigate certain unforeseen systematic error contributions, the pattern used for multiple measurements may be randomized rather than arranged in a perfectly ordered matrix. This can also be done with multiple before and after process effect measurements.

Other statistical calculations may alternatively be used to calculate the number of measurements N needed. For example, Equation 1 may be used to calculate N for measurements following normal distributions:

Equation 1:
$$N = \frac{\sigma * U_a}{(RI^{True} - RI^{Av})^2}$$

where $RI^{True}$ is the refractive index calculated using a prior art method of a stable film, $RI^{Av}$ is the refractive index of a plurality of measurements made at a reduced dose of radiation in accordance with an embodiment of the present invention, σ is the square root of the population variance, and $U_\alpha$ is the Student T statistic with the appropriate degrees of freedom and alpha risk. Note that other statistical formulas are suitable for calculating the number of measurements needed for other types of distributions, for example.

An example of calculating the number of measurements N required to measure the index of refraction of a film 204 will next be described. Assuming that the measurement of the refractive index with a prior art high radiation dose of a stable film is the true value, $RI^{True}$, and that measurements of the refractive index taken at low radiation dose according to an embodiment of the present invention are normally distributed. For example, the standard deviation of measurements of the refractive index under low radiation dose conditions is assumed to be 0.001 units. Assume also that it is desired that the average measurement ($RI^{Av}$) is within 0.0005 units. The null hypothesis is that the average measurement under low radiation dose conditions is not within 0.0005 units assuming a two tailed normal distribution with 2.5% under each tail. The number of measurements N may be calculated using Equation 1, where ($RI^{Tru}-RI^{Av}$)=0.0005 units, σ=0.001, and $U_\alpha$=T statistic with (N−2) degrees of freedom. Some iteration may be necessary because $U_\alpha$ is a function of N. For example, first it may be assumed that N is very large. One would look up $U_\alpha$ in a statistical table, and then calculate the number of measurements N. One may then look up $U_\alpha$ for (N−2) degrees of freedom and recalculate the number of measurements N. This may be repeated until the number of measurements calculated Integer ($N_{calc}$) is constant. Calculations for the above example and assumptions are shown in Table 1:

TABLE 1

| N | N-2 | $U_{\alpha(N-2)}$ | $N_{calc}$ | Integer($N_{calc}$) |
|---|---|---|---|---|
| Very Large | Very Large | 1.96 | 15.3664 | 15 |
| 15 | 13 | 2.17 | 18.8356 | 19 |
| 19 | 17 | 2.11 | 17.8084 | 18 |
| 18 | 16 | 2.12 | 17.9776 | 18 |

Embodiments off the present invention include a method of measuring an optical property of a film (see FIG. 9) and a system 201 (see FIG. 3) for measuring an optical property of a film. A further embodiment includes an algorithm and/or software program for measuring an optical property of a film, for example. The actinic radiation sensitivity dose of a film may be programmed into the processor 213, as well as the precision and accuracy of the measurements, as examples. The spot size (or size of the measurement location) and the percentage of the actimic radiation sensitivity dose to be used during the measurements may be input to or calculated by the processor 213. The number of measurements N and the accuracy or offset 258 may be input to the processor 213, or the processor 213 may calculate these values, for example.

Embodiments of the present invention are particularly useful in the measurement of materials or films 204 that are chemically amplified, such as chemically amplified 157 nm sensitivity resists, wherein "157 nm" indicates the wavelength at which the resist is exposed, or the actimic radiation sensitivity dose. Another example of a chemically amplified film is chemically amplified 193 nm sensitive resist, as an example. These types of radiation sensitive resists are designed to have a large chemical change upon a small dose of radiation. However, embodiments of the present invention are also useful in the measurement of other less radiation sensitive resists and other stable films used in semiconductor device manufacturing.

Advantages of embodiments of the invention include providing the ability to accurately measure optical properties of radiation sensitive film 204 without causing chemical changes in the film 204. Many measurements are taken at low, short doses in very close proximity to one another, e.g., at locations 216a, 216b, 216c, etc., in a particular region 206 of the film 204, (see FIG. 5) so that the signal-to-noise ratio is lower than if measuring optical properties of films that are stable. Optical properties such as the index of refraction, thickness of a film, the absorption of the film, and the speed of light through the film, as examples, may be measured using embodiments of the present invention.

The plurality of low-dose measurements may be taken in a plurality of regions 206 across a surface of a workpiece 202 (see FIG. 6) to determine the variation of the refractive index of a film 204 across the surface of a workpiece 202, for example. The measurements taken in accordance with embodiments of the present invention may be used in simulation of lithography of the measured films for modeling purposes, for example.

By distributing the measurement dose of radiation across a larger surface area of the surface of a film in accordance with embodiments of the present invention, chemical changes to the film caused by the measurements of the film are avoided.

Although embodiments of the present invention and their advantages have been described in detail, it should be understood that various changes, substitutions and alterations can be made herein without departing from the spirit and scope of the invention as defined by the appended claims. For example, it will be readily understood by those skilled in the art that many of the features, functions, processes, and materials described herein may be varied while remaining within the scope of the present invention. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of measuring an optical property of a film, the method comprising:
    providing a workpiece, the workpiece having a film disposed thereon;
    measuring an optical property of the film at a first location of the film;
    moving the film so that an optical property can be measured in at least on second location;
    measuring the optical property of the film at said at least one second location, each at least one second location being proximate and different from the first location, the first location and the at least one second location comprising a first region of the film; and
    averaging the optical property measurement of the film in the first location and the optical property measurement of the film in the at least one second location of the film to determine an average optical property measurement of the first region of the film.

2. The method according to claim 1, wherein the first optical property measurement and the at least one second optical property measurement comprise the refractive index of the film.

3. The method according to claim 1, wherein the first optical property measurement and the at least one second optical property measurement comprise the thickness of the film, the absorption of the film, or the speed of light through the film.

4. The method according to claim 1, wherein measuring the first optical property of the film and measuring the at least one second optical property of the film comprise irradiating the workpiece in the first location and the at least one second location, respectively, with energy.

5. The method according to claim 4, wherein the film comprises a radiation sensitive film, the radiation sensitive film being chemically alterable by an actinic radiation sensitivity dose.

6. The method according to claim 5, wherein measuring the optical property of the film in the first location and measuring the optical property of the film in the at least one second location is at a dose of about 50 to 90% of the actinic radiation sensitivity dose.

7. The method according to claim 5, wherein the radiation sensitive film comprises a radiation sensitive resist.

8. A method of measuring an optical property of a film, the method comprising:
    providing a workpiece, the workpiece having a film disposed thereon;
    measuring an optical property of the film in a first location;
    measuring the optical property of the film in at least one second location, each second location being proximate and different from the first location, the first location and the at least one second location comprising a first region of the film;
    averaging the optical property measurement of the film in the first location and the optical property measurement of the film in the at least one second location of the film to determine an average optical property measurement of the first region of the film;
    measuring an optical property of the film in a third location;
    measuring the optical property of the film in at least one fourth location, each fourth location being proximate and different from the third location, the third location and the at least one fourth location comprising a second region of the film; and
    averaging the optical property measurement of the film in the third location and the optical property measurement of the film in at least one fourth location of the film to determine an average optical property measurement of the second region of the film.

9. The method according to claim 8, wherein the film comprises a plurality of fourth locations within the second region, wherein each fourth location is proximate and different from every other fourth location.

10. The method according to claim 8, further comprising:
    determining an average optical property measurement of at least one third region of the film.

11. A method of measuring an optical property of a film, the method comprising:
    providing a workpiece, the workpiece having a film disposed thereon;
    measuring an optical property of the film in a first location;
    measuring the optical property of the film in at least one second location, each second location being proximate and different from the first location, the first location and the at least one second location comprising a first region of the film;
    averaging the optical property measurement of the film in the first location and the optical property measurement of the film in the at least one second location of the film to determine an average optical property measurement of the first region of the film; and
    determining the total number of measurement locations N of the first location and the at least one second location according the Equation:

$$N = \frac{\sigma * U_a}{(RI^{True} - RI^{Av})^2}$$

where $RI^{True}$ is an optical property of a stable film measured with a high radiation dose, $RI^{Av}$ is the average optical property of the film in the first region, $\sigma$ is the square root of the population variance, and $U_\alpha$ is the Student T statistic with the appropriate degrees of freedom for a given alpha risk.

12. A method of measuring an optical property of a film, the method comprising:
    providing a workpiece, the workpiece having a first film disposed thereon;
    measuring an optical property of the first film in a first location;
    measuring the optical property of the first film in at least one second location, each second location being proximate and different from the first location, the first location and the at least one second location comprising a first region of the film and wherein measuring the optical property of said first film at said first and second locations comprises using a first radiation dose;
    averaging the optical property measurement of the film in the first location and the optical property measurement of the film in the at least one second location of the film to determine an average optical property measurement of the first region of the film;
    measuring the optical property of a second film with a second radiation dose, the second radiation dose being higher than the first radiation dose; and comparing the measured optical property of the second film and the average optical property measurement of the first region of the first film, wherein a difference in the comparison comprises a calibration factor.

13. The method according to claim 12, further comprising:
measuring an optical property of a third film in a first location;
measuring the optical property of the third film in at least one second location, each second location being proximate and different from the first location, the first location and the at least one second location comprising a first region of the third film; and
averaging the optical property of the third film in the first location and the optical property of the third film in the at least one second location of the third film to determine an average optical property measurement of the first region of the third film; and
adjusting the average optical property measurement of the first region of the third film by the calibration factor.

14. The method according to claim 1, further comprising:
determining an actinic radiation sensitivity dose of the film;
providing a radiation transceiver;
reducing a radiation dose emitted from the radiation transceiver to a reduced radiation dose, the reduced radiation dose being less than the actinic radiation sensitivity dose of the film; and
measuring the optical property of the film in the first location and the at least one second location using the reduced radiation dose.

15. The method according to claim 14, wherein reducing the radiation dose is accomplished by a radiation reducer or a radiation adjustor.

16. The method according to claim 15, wherein the radiation reducer comprises a screen, aperture in an opaque material, or a filter.

17. The method according to claim 14, wherein the reduced radiation dose comprises light, ultraviolet light, electrons, or x-rays.

18. A system for measuring an optical property of a film, the system comprising:
a radiation reduction element;
a radiation transceiver disposed proximate the radiation reduction element, the radiation transceiver including a radiation transmitter for emitting a radiation dose towards a film disposed on a device, the radiation transceiver including a radiation detector for measuring reflected radiation from the film in a first location and in at least one second location using a reduced radiation dose, each second location being proximate and different from the first location, the first location and the at least one second location comprising a first region of the film, the reduced radiation dose comprising the radiation dose emitted from the radiation transceiver reduced by the radiation reduction element;
apparatus for providing relative motion between said radiation transceiver and said film from said fist location to said at least one second location; and
a processor, wherein the processor is adapted to average the measured optical property of the film in the first location and the measured optical property of the film in the at least one second location to determine an average optical property measurement of the first region of the film.

19. The system according to claim 18, wherein the reduction element comprises a radiation reducer or an adjustment means.

20. The system according to claim 19, wherein the radiation reducer comprises a screen, aperture in an opaque material, or a filter.

21. The system according to claim 18, wherein the reduced radiation dose comprises light, ultraviolet light, electrons, or x-rays.

22. The system according to claim 18, wherein the measured optical property comprises the refractive index of the film, the thickness of the film, the absorption of the film, or the speed of light through the film.

23. The system according to claim 18, wherein the film comprises a radiation sensitive film, the radiation sensitive film being chemically alterable by an actinic radiation sensitivity dose, wherein the radiation reduction element is adapted to reduce the radiation emitted from the radiation transceiver to a reduced radiation dose comprising about 50 to 90% of the actinic radiation sensitivity dose.

24. A system for measuring an optical property of a film, the system comprising:
a radiation reduction element;
a radiation transceiver disposed proximate the radiation reduction element, the radiation transceiver including a radiation transmitter for emitting a radiation dose towards a film disposed on a device, the radiation transceiver including a radiation detector for measuring reflected radiation from the film in a first location and in at least one second location using a reduced radiation dose, each second location being proximate and different from the first location, the first location and the at least one second location comprising a first region of the film, the reduced radiation dose comprising the radiation dose emitted from the radiation transceiver reduced by the radiation reduction element;
a processor, wherein the processor is adapted to average the measure optical property of the film in the first location and the measured optical property of the film in the at least one second location to determine and average optical property measurement of the first region of the film; and
wherein the processor is adapted to determine the total number of measurement locations N of the first location and the at least one second location according to the Equation:

$$N = \frac{\sigma * U_a}{(RI^{True} - RI^{Av})^2}$$

where $RI^{True}$ is an optical property of a stable film measured with a high radiation dose, $RI^{Av}$ is the average optical property of the film in the first region, $\sigma$ is the square root of the population variance, and $U_\alpha$ is the Student T statistic with the appropriate degrees of freedom for a given alpha risk.

25. A system for measuring an optical property of a film, the system comprising:
means for transmitting radiation towards a film disposed on a device;
means for controllably reducing the radiation transmitted from the means for transmitting radiation;
means for measuring radiation transmitted from the means for transmitting radiation, reduced by the means for controllably reducing the radiation and reflected from the film disposed on the device in a first location and in at least one second location, each second location being proximate and different from the first location, each second location being proximate and different from every other second location, the first location and the at least one second location comprising a first region of the film;

means for providing relative motion between said means for transmitting radiation and said film from said first location to said at least one second location; and means for averaging the measured optical property of the film in the first location and the measured optical property of the film in the at least one second location to determine an average optical property measurement of the first region of the film.

26. The system according to claim 25, wherein the film is chemically altered at an actinic radiation sensitivity dose, wherein the means for controllably reducing the radiation transmitted from the means for transmitting radiation is adapted to reduce the radiation from the means for transmitting radiation to about 50 to 90% of the actinic radiation sensitivity dose of the film.

27. The system according to claim 25, wherein the measured optical property comprises the refractive index of the film, the thickness of the film, the absorption of the film, or the speed of light through the film.

28. The system according to claim 25, wherein the reduced radiation dose comprises light, ultraviolet light, electrons, or x-rays.

29. A method of measuring an optical property of a film, the method comprising:

providing a workpiece, the workpiece having a film disposed thereon;

measuring an optical property of the film in a first location of a first region of the film;

measuring the optical property of the film in a plurality of second locations of said first region, each second location of said first region being proximate and different from the first location and proximate and different from every other second location; and averaging the optical property measurement of the film in the first location and the optical property measurement of the film in the at least one second location of the film to determine an average optical property measurement of the first region of the film.

30. A system for measuring an optical property of a film, the system comprising:

a radiation reduction element;

a radiation transceiver disposed proximate the radiation reduction element, the radiation transceiver including a radiation transmitter for emitting a radiation dose towards a film disposed on a device, the radiation transceiver including a radiation detector for measuring reflected radiation from the film in a first location and in a plurality of second locations using a reduced radiation dose, each second location being proximate and different from the first location and proximate end different from every other second location, the first location and the plurality of second locations comprising a first region of the film, the reduced radiation dose comprising the radiation dose emitted from the radiation transceiver reduced by the radiation reduction element; and a processor, wherein the processor is adapted to average the measured optical property of the film in the first location and the measured optical property of the film in the plurality of second locations to determine an average optical property measurement of the first region of the film.

* * * * *

UNITED STATES PATENT AND TRADEMARK OFFICE
CERTIFICATE OF CORRECTION

| | |
|---|---|
| PATENT NO. | : 7,099,018 B2 |
| APPLICATION NO. | : 10/755420 |
| DATED | : August 29, 2006 |
| INVENTOR(S) | : Ziger |

Page 1 of 1

It is certified that error appears in the above-identified patent and that said Letters Patent is hereby corrected as shown below:

Column 13, line 11; delete "least on second" insert --least one second--
Column 15, line 58; delete "said fist" insert --said first--

Signed and Sealed this

Twenty-eighth Day of November, 2006

JON W. DUDAS
*Director of the United States Patent and Trademark Office*